US011493755B2

(12) United States Patent
Yamane et al.

(10) Patent No.: US 11,493,755 B2
(45) Date of Patent: Nov. 8, 2022

(54) MICROSCOPE DRAPE

(71) Applicant: MEILLEUR CO., LTD., Funabashi (JP)

(72) Inventors: Tsurashi Yamane, Funabashi (JP); Kaori Nakagawa, Funabashi (JP); Junko Ochibe, Funabashi (JP)

(73) Assignee: MEILLEUR CO., LTD., Funabashi (JP)

( * ) Notice: Subject to any disclaimer, the term of this patent is extended or adjusted under 35 U.S.C. 154(b) by 0 days.

(21) Appl. No.: 17/049,747

(22) PCT Filed: Jun. 30, 2020

(86) PCT No.: PCT/JP2020/025619
§ 371 (c)(1),
(2) Date: Oct. 22, 2020

(87) PCT Pub. No.: WO2022/003806
PCT Pub. Date: Jan. 6, 2022

(65) Prior Publication Data
US 2021/0405353 A1 Dec. 30, 2021

(51) Int. Cl.
*G02B 27/00* (2006.01)
*G02B 21/00* (2006.01)

(52) U.S. Cl.
CPC ...... *G02B 27/0006* (2013.01); *G02B 21/0012* (2013.01)

(58) Field of Classification Search
CPC ............ G02B 21/0012; G02B 27/0006; G02B 21/24; G02B 21/00; G02B 21/22;
(Continued)

(56) References Cited

U.S. PATENT DOCUMENTS 5,367,742 A * 11/1994 Bindman ............. A47H 13/02
16/87.2
6,318,864 B1 * 11/2001 Fukaya .............. G02B 21/0012
359/368

(Continued)

FOREIGN PATENT DOCUMENTS

JP 2000-024002 A 1/2000
JP 2006292033 A * 10/2006
(Continued)

OTHER PUBLICATIONS

Apr. 6, 2021 European Search Report issued in European Patent Application No. 20 78 9434.6.
(Continued)

*Primary Examiner* — Stephone B Allen
*Assistant Examiner* — Rahman Abdur
(74) *Attorney, Agent, or Firm* — Oliff PLC

(57) ABSTRACT

A microscope drape with a structure in which a distance between an objective lens and a surgical field is appropriately set includes: a lens cap attached to or detached from a housing of an objective lens of a surgical microscope; a protective lens attached to a distal end of the lens cap in a state of being inclined with respect to an optical axis of the objective lens to protect the objective lens; a drape body attached to an outer periphery of the protective lens to cover, together with the lens cap, the surgical microscope; and a joint that supports the protective lens with respect to the lens cap so as to change an inclination angle of the protective lens with respect to the optical axis.

15 Claims, 11 Drawing Sheets

(58) Field of Classification Search
CPC ...... G02B 21/18; G02B 21/082; A61B 46/10;
A61B 90/20; A61B 19/081; A61B 3/132;
A61B 3/117; A61B 90/25; A61B 3/13;
A61B 1/00149; A61B 1/045; A61B 1/00142
USPC ........................................................ 359/510
See application file for complete search history.

(56) References Cited

U.S. PATENT DOCUMENTS

| | | | |
|---|---|---|---|
| 6,484,788 B1* | 11/2002 | Jerrell | A47H 13/02 16/87.2 |
| 7,182,474 B2* | 2/2007 | Fuchs | A61B 46/10 359/510 |
| 8,864,320 B2* | 10/2014 | Chua | G02B 27/0006 359/510 |
| 10,603,217 B2* | 3/2020 | Spier | A61B 34/37 |
| 2004/0190140 A1 | 9/2004 | Bala | |
| 2005/0063058 A1 | 3/2005 | Langley | |
| 2005/0286130 A1 | 12/2005 | Bala | |
| 2008/0144178 A1 | 6/2008 | Dillon et al. | |
| 2010/0238551 A1 | 9/2010 | Hubbs | |
| 2013/0329291 A1 | 12/2013 | Federle | |
| 2014/0240832 A1 | 8/2014 | Nakamura et al. | |
| 2017/0168292 A1 | 6/2017 | Koenig et al. | |
| 2018/0341167 A1* | 11/2018 | Martinez | G03B 11/041 |
| 2020/0187754 A1 | 6/2020 | Furukawa et al. | |

FOREIGN PATENT DOCUMENTS

| | | |
|---|---|---|
| JP | 2008-545506 A | 12/2008 |
| JP | 2010-512851 A | 4/2010 |
| JP | 2012-183449 A | 9/2012 |
| JP | 2014-161504 A | 9/2014 |
| JP | 2017-107210 A | 6/2017 |
| KR | 10-2009-0101922 A | 9/2009 |
| WO | 2019/023390 A2 | 1/2019 |
| WO | 2019/044754 A1 | 3/2019 |
| WO | 2020/009731 A1 | 1/2020 |

OTHER PUBLICATIONS

Dec. 9, 2020 Office Action issued in Taiwanese Patent Application No. 109130284. (with partial translation).
Oct. 26, 2020 Office Action issued in Korean Patent Applicatioin No. 10-2020-7024419 (with partial tanslation).
Aug. 4, 2020 Written Opinion issued in International Patent Application No. PCT/JP2020/025619.
Aug. 4, 2020 International Search Report issued in International Patent Application No. PCT/JP2020/025619.

* cited by examiner

MICROSCOPE DRAPE

TECHNICAL FIELD

The present invention relates to a microscope drape for covering a surgical microscope.

BACKGROUND ART

Conventionally, in neurosurgery and ophthalmology, there have been cases that surgery is performed while enlarging a surgical field by using a surgical microscope. Since it is difficult to sterilize the surgical microscope itself, it is general to cover the surgical microscope with a microscope drape which is disposable for each operation (see, e.g., Patent Literatures 1 to 4)

Such a microscope drape includes a lens cap which is attached to or detached from an objective lens of the surgical microscope. In addition, as mentioned in Patent Literature 3 and Patent Literature 4, in order to prevent illumination light from entering the objective lens and causing an operator to feel dazzling (hereinafter referred to as "glare"), there are cases that a protective lens inclined with respect to an optical axis of the objective lens is attached to the lens cap.

CITATION LIST

Patent Literature

Patent Literature 1: JP-A-2012-183449
Patent Literature 2: JP-A-2014-161504
Patent Literature 3: JP-T-2010-512851
Patent Literature 4: JP-A-2017-107210

SUMMARY OF INVENTION

Technical Problem

However, in the microscope drape configured as above, since the lens cap protrudes from the objective lens, there is a problem that the microscope drape becomes an obstacle for the surgery. Particularly, since the lens cap provided with the protective lens is increased in size, the problem descried above becomes conspicuous. In addition, since it is necessary to firmly fix the large-sized lens cap to the objective lens so as not to fall out therefrom by its own weight, there is another problem that large force is required for attachment/detachment of the microscope drape.

The present invention has been made to solve the problems above in the prior art, and an object of the present invention is to provide a microscope drape with a structure in which a distance between an objective lens and a surgical field is appropriately set to ensure a surgical manipulation space for an operator.

Solution to Problem

In order to solve the problems above, the present invention provides a microscope drape for covering a surgical microscope, comprising: a lens cap that is attached to or detached from a housing of an objective lens of the surgical microscope; a protective lens that is attached to a distal end of the lens cap in a state of being inclined with respect to an optical axis of the objective lens to protect the objective lens; a drape body that is attached to an outer periphery of the protective lens to cover, together with the lens cap, the surgical microscope; and a joint that supports the protective lens with respect to the lens cap so as to change an inclination angle of the protective lens with respect to the optical axis.

Advantageous Effects of Invention

According to the present invention, it is possible to provide a microscope drape with a structure in which a distance between an objective lens and a surgical field is appropriately set to ensure a surgical manipulation space for an operator.

DESCRIPTION OF EMBODIMENTS

Hereinafter, a microscope drape 10 according to the present embodiment will be described with reference to the drawings. It should be noted that the embodiment described below of the present invention shows an example in which the present invention is embodied, but does not limit the scope of the present invention to the scope of the description of the embodiment. Accordingly, the present invention may be implemented by adding various modifications to the embodiment.

Figure 1:
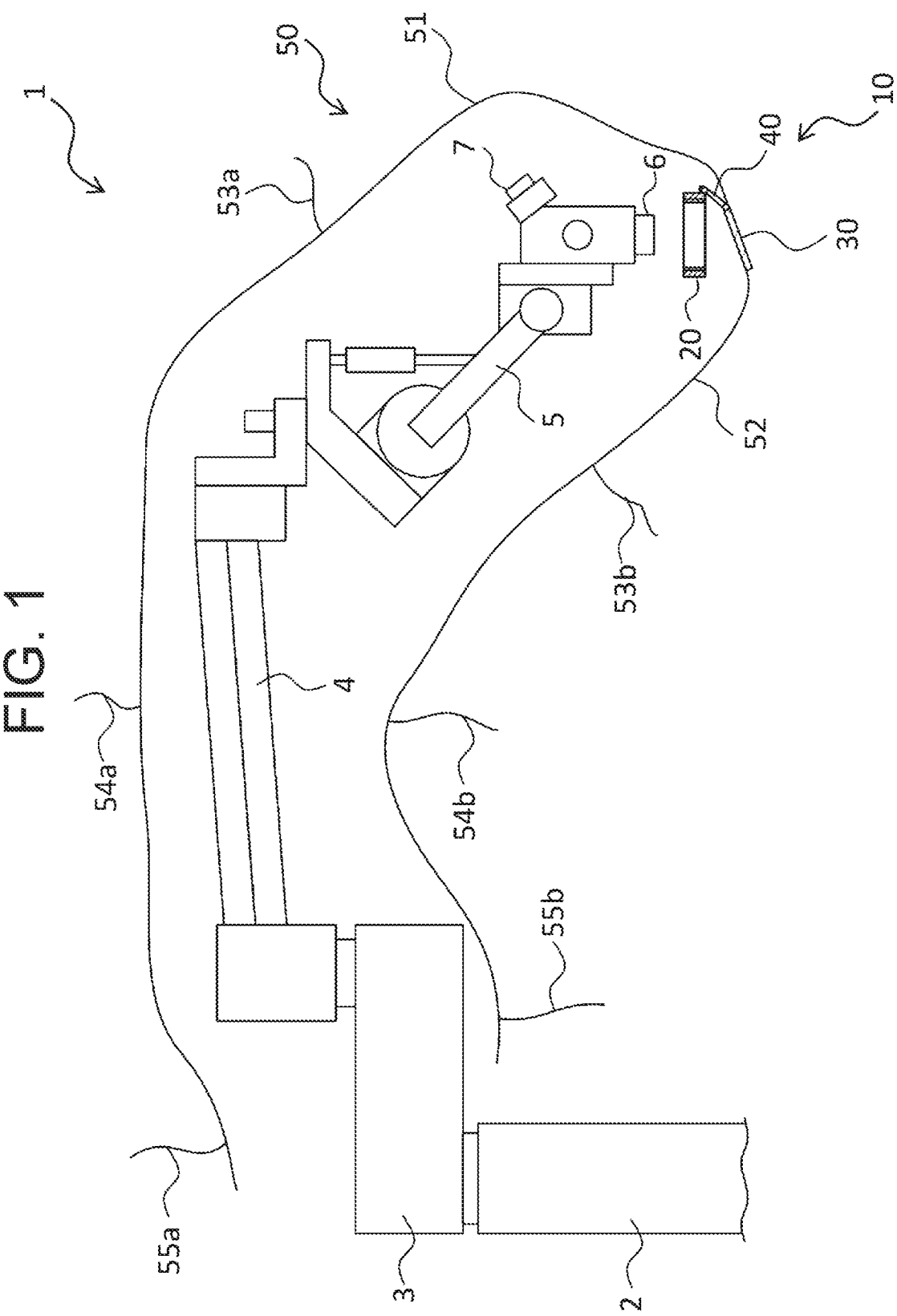
FIG. 1 is an overview schematic diagram of a main part of a surgical microscope and a microscope drape.
Figure 2:
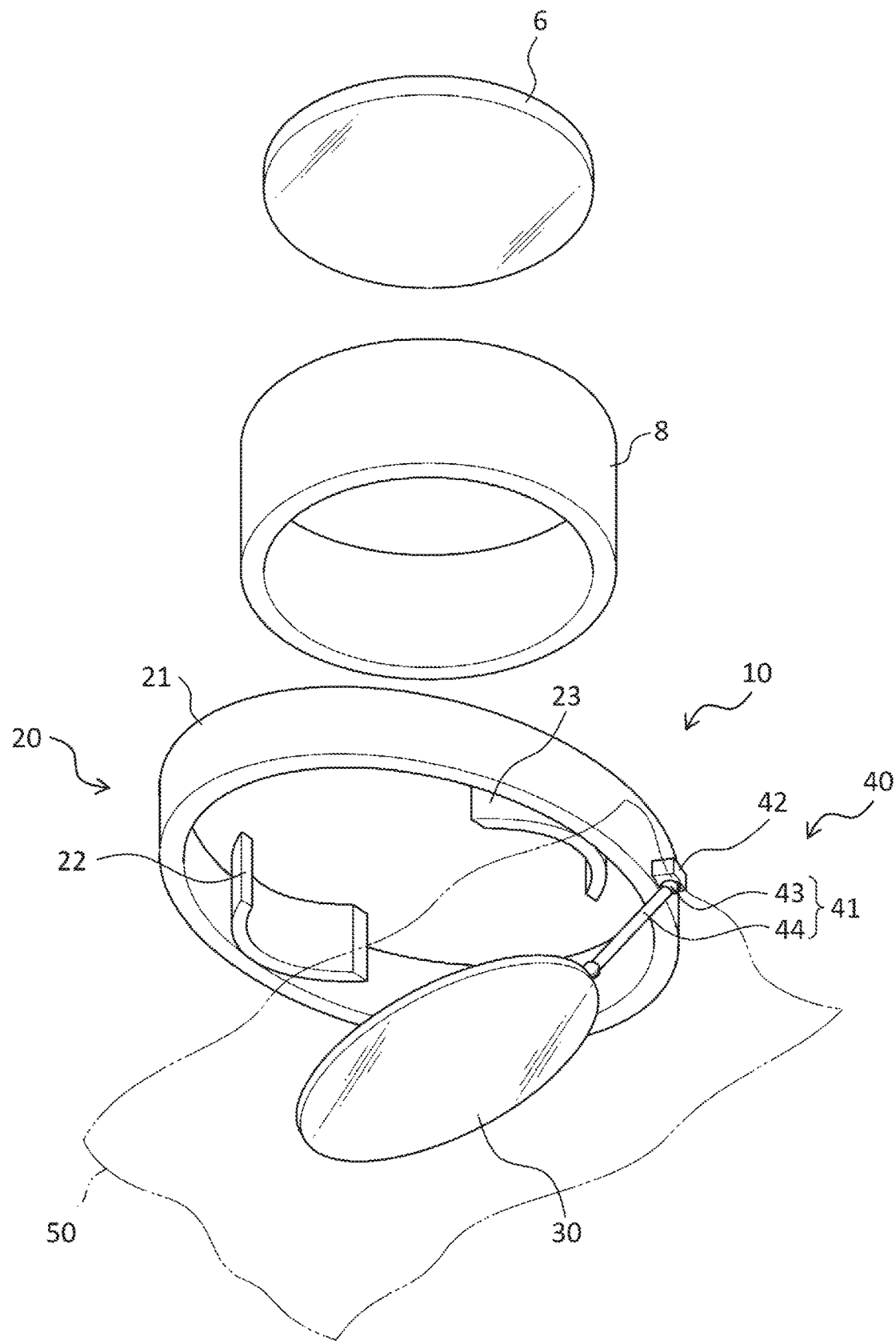
FIG. 2 is an exploded perspective diagram of an objective lens and a microscope drape.
Figure 3:
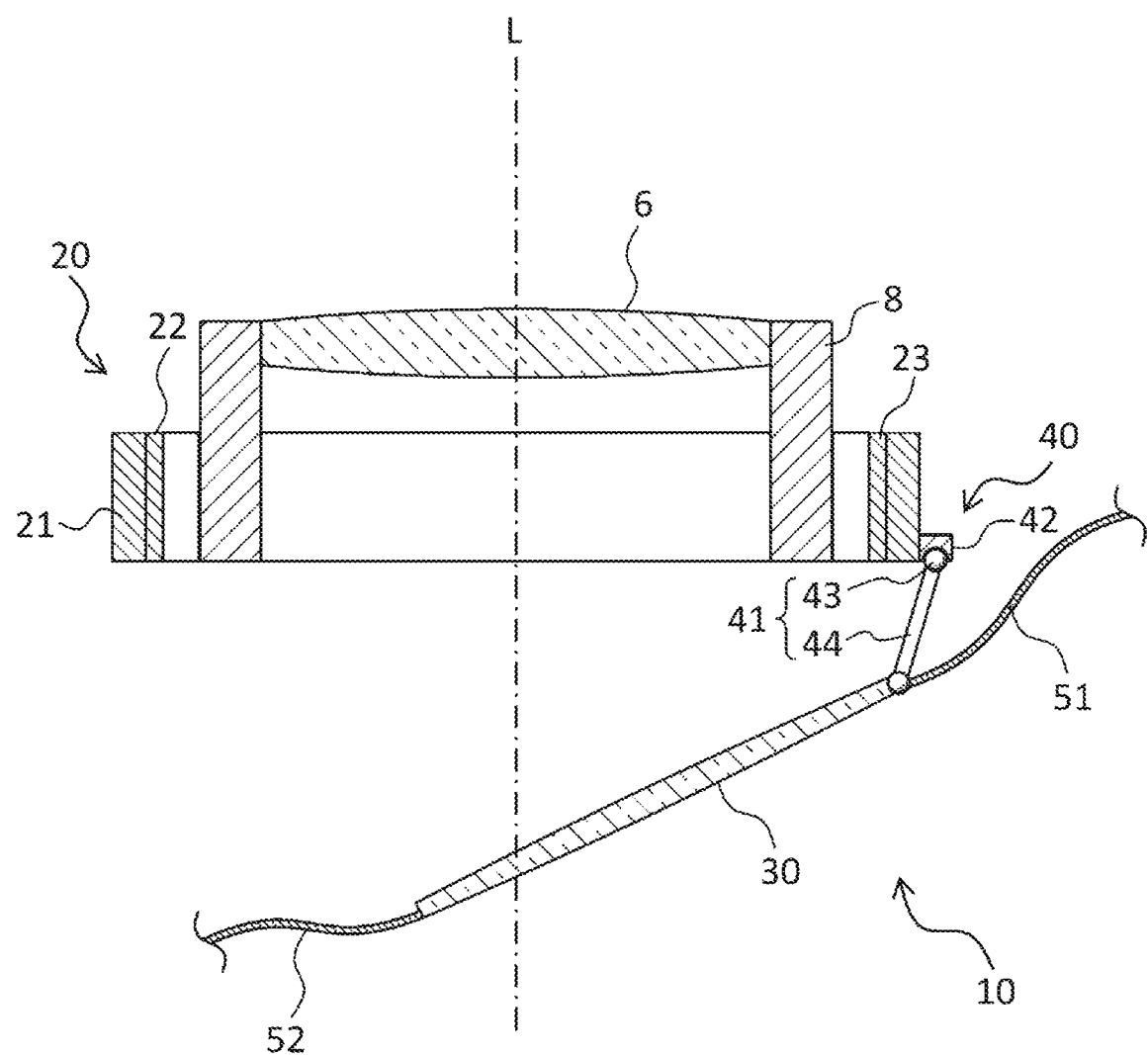
FIG. 3 is a cross-section diagram of an objective lens and a microscope drape.

FIG. 1 is an overview schematic diagram of a main part of a surgical microscope 1 and a microscope drape 10. FIG. 2 is an exploded perspective diagram of an objective lens 6 and the microscope drape 10. FIG. 3 is a cross-section diagram of the objective lens 6 and the microscope drape 10.

As illustrated in FIG. 1, the surgical microscope 1 mainly includes arms 2, 3, 4, 5 that are rotatably connected to each other, and the objective lens 6 and an eyepiece lens 7 that are attached to a distal end of the arm 5. Joint portions of the arms 2 to 5 are relatively rotated to each other so that the objective lens 6 is allowed to be located at a position facing a surgical field. With this configuration, a surgeon (doctor) can observe an enlarged surgical field by looking into the eyepiece lens 7.

As illustrated in FIG. 2 and FIG. 3, the objective lens 6 is a convex lens. The objective lens 6 is attached to the inside of a cylindrical shaped housing 8. That is, an optical axis L of the objective lens 6 illustrated by a dashed line in FIG. 3 coincides with an axial direction of the housing 8.

In addition, the surgical microscope 1 includes an illumination device (an LED, a xenon lamp, etc.). Light emitted from the illumination device passes through the objective lens 6 via an optical system (lens, mirror, etc.) accommodated in the arms 2 to 5, and then is irradiated toward the surgical field. This light is reflected by the surgical field and is made incident on the objective lens 6 again, whereby the doctor can observe the surgical field. An irradiation direction of the light by the illumination device is inclined about, for example, 3° to 6° with respect to the optical axis L.

All instruments touching or potentially touching a surgical site during surgery must be sterilized. However, since it is difficult to sterilize the surgical microscope 1 itself, the surgical microscope 1 is covered with the microscope drape 10 that is disposable for each operation. The microscope drape 10 has been packaged in a sterilized state, and is unpackaged in an operating room and made to cover the surgical microscope 1. As illustrated in FIGS. 1 to 3, the microscope drape 10 mainly includes a lens cap 20, a protective lens 30, a joint 40, and a drape body 50.

The lens cap 20 is attached to or detached from the housing 8 of the objective lens 6, and serves to support the protective lens 30. The lens cap 20 is integrally formed of, for example, resin having elastic deformability. As the resin forming the lens cap 20, for example, polycarbonate or polyacetal can be employed. As illustrated in FIG. 2 and FIG. 3, the lens cap 20 mainly includes a cylindrical body 21 and a pair of arc portions 22, 23.

The cylindrical body 21 has a cylindrical outer shape with both ends being opened. The cross-section of the cylindrical body 21 (cross-section perpendicular to the axial direction) is an elliptical shape having a major axis-a and a minor axis-b (see FIG. 4). Meanwhile, the shape of the cross-section of the cylindrical body 21 is not limited to an ellipse in a strict sense defined geometrically as long as being a flat circular shape.

The cylindrical body 21 is formed to be elastically deformable. More particularly, the cylindrical body 21 is elastically deformable so that the length of the major axis-a and the length of the minor axis are changed. That is, the shape of the cross-section of the cylindrical body 21 may be elastically deformed to form a true circle as long as being a flat circle in its natural state (state of not being elastically deformed).

Each of the arc portions 22, 23 has an arc-shaped outer form. The arc portions 22, 23 are fixed to the inside of the cylindrical body 21 so as to face each other in the direction of the minor axis-b. More particularly, an outer peripheral surface of each of the arc portions 22, 23 is attached to an inner peripheral surface of the cylindrical body 21. Furthermore, the arc portions 22, 23 are arranged such that inner peripheral surfaces thereof face each other. Still further, each of the arc portions 22, 23 is elastically deformable so as to increase or reduce the radius of curvature.

The protective lens 30 is a plate-like shaped lens formed of a material that transmits light (glass, resin, etc.). In this connection, the form of the protective lens 30 is not limited to a flat plate, but a curved lens that protrudes in a convex shape may be adopted. The protective lens 30 is attached to a distal end of the lens cap 20 via the joint 40. The protective lens 30 protects the objective lens 6. More specifically, in a state where the lens cap 20 is attached to the housing 8, the protective lens 30 faces the objective lens 6, whereby external light passing through the protective lens 30 is incident on the objective lens 6.

The joint 40 is supported on an outer periphery of a distal end of the cylindrical body 21 to support the protective lens 30. The joint 40 supports the protective lens 30 with respect to the lens cap 20 so that an inclination angle with respect to the optical axis L can be changed. That is, as illustrated in FIG. 3, the protective lens 30 can be held in a state of being inclined with respect to the optical axis L.

The joint 40 according to the present embodiment is a so-called "ball joint" including a ball stud 41 and a socket 42. The ball stud 41 includes a ball 43 and a rod 44 protruding from a surface of the ball 43. The socket 42 rotatably supports the ball 43. The socket 42 is attached to the distal end of the cylindrical body 21, thereby supporting the protective lens 30 at a distal end of the rod 44. In this connection, the specific structure of the joint 40 is not limited to the above, while the protective lens 30 may be directly fitted to the lens cap 20 without providing the joint 40.

The drape body 50 is a sheet-like member. As illustrated in FIGS. 1 to 3, the drape body 50 is attached to an outer periphery of the protective lens 30. In other words, the drape body 50 includes an opening from which the protective lens 30 is exposed. The drape body 50 according to the present embodiment includes a first drape 51, a second drape 52, and a plurality of strings 53a, 53b, 54a, 54b, 55a, 55b (tying portions). In this connection, the number of the strings 53a, 53b, 54a, 54b, 55a, 55b which function as the tying portions is not limited to the example illustrated in FIG. 1, but a single or a plurality of strings may be provided.

Each of the first drape 51 and the second drape 52 is a long strip-shaped sheet. One end of each of the first drape 51 and the second drape 52 is attached to the protective lens 30 such that the first drape 51 and the second drape 52 extend in mutually different directions. By attaching the lens cap 20 to the housing 8, one of the upper part and the lower part of the surgical microscope 1 can be covered with the first drape 51, and the other of the upper part and the lower part of the surgical microscope 1 can be covered with the second drape 52.

The strings 53a, 54a, 55a are attached to a side part (outer periphery) of the first drape 51. The strings 53b, 54b, 55b are attached to a side part (outer periphery) of the second drape 52. By winding the strings 53a, 53b, 54a, 54b, 55a, 55b around the surgical microscope 1 and tying them in a state where the side part of the first drape 51 and that of the second drape 52 are overlapped with each other, the drape body 50 is tied to the surgical microscope 1. As a result, it is possible to prevent the drape body 50 from sagging and the surgical microscope 1 from being exposed. In this connection, the specific structure of the tying portion is not limited to the example above, while a snap button, a zipper fastener, a hook and loop fastener, a rubber string to be wound around the surgical microscope 1 so as to tie the drape body 50 thereto, etc. may be adopted.

On the other hand, the drape body 50 is not provided with a concavo-convex portion into which the eyepiece lens 7 is inserted. The first drape 51 and the second drape 52 are smooth sheets. An arbitrary position (first drape 51 in the example of FIG. 1) of the drape body 50 which covers the surgical microscope 1 is fixed to a periphery of the eyepiece lens 7 with a rubber band, etc. Then, a portion of the drape body 50 which covers the eyepiece lens 7 is cut in accordance with the outer diameter of the eyepiece lens 7, thereby allowing the eyepiece lens 7 to be exposed.

Figure 4A:
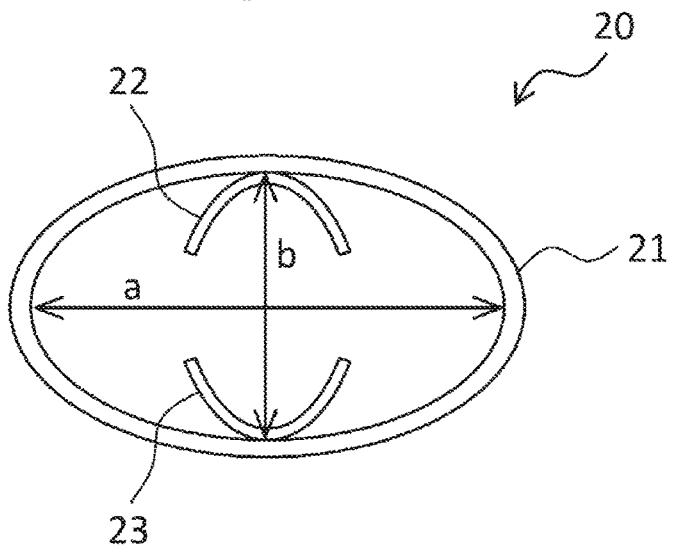
FIG. 4A illustrates a lens cap in its natural state.

Next, a procedure for attaching the microscope drape 10 to the surgical microscope 1 will be described. FIG. 4 explains a procedure for attaching the lens cap 20 to the housing 8.

Figure 4B:
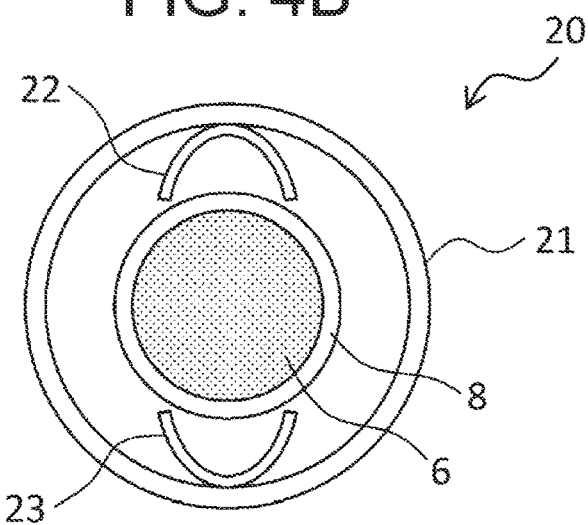
FIG. 4B illustrates a lens cap which is elastically compressed in a direction of shortening a major axis-a.

First, an operator (e.g., a doctor, a nurse, or any other person who prepares for surgery) elastically compresses the lens cap 20 in a direction of the major axis-a of the cylindrical body 21. Thus, as illustrated in FIG. 4B, the major axis-a is shortened while the minor axis-b becomes longer, which makes the shape of the cross-section of the cylindrical body 21 similar to a true circle. More particularly, the operator elastically compresses the lens cap 20 until both the length of the major axis-a and the minor axis-b becomes greater than the diameter of the housing 8.

Next, as illustrated in FIG. 4B, the operator fits the elastically compressed lens caps 20 onto the housing 8. Then, after fitting the lens cap 20 onto the housing 8, the operator removes the compressive force acting on the lens cap 20. Thus, the cylindrical body 21 is elastically restored in a direction in which the major axis-a becomes longer while the minor axis-b is shortened. Here, it is assumed that the major axis-a of the cylindrical body 21 fitted onto the housing 8 is shorter than the major axis-a in its natural state. In other words, it is assumed that the minor axis-b of the cylindrical body 21 fitted onto the housing 8 is longer than the minor axis-b in its natural state.

Figure 4C:
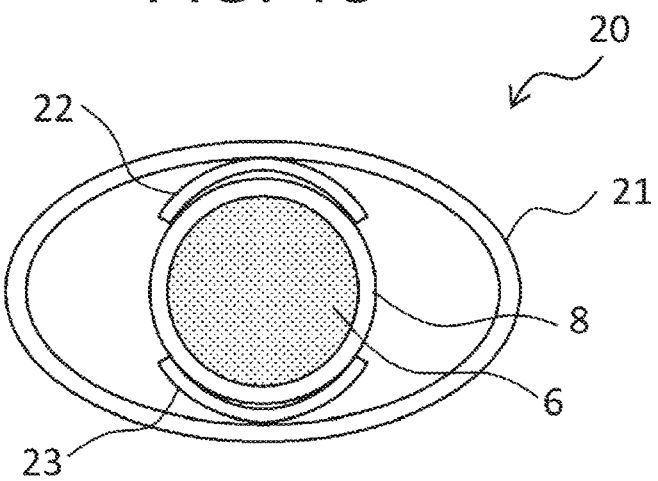
FIG. 4C illustrates a state where a lens cap is attached to a housing.

Thus, as illustrated in FIG. 4C, each of the inner peripheral surfaces of the pair of arc portions 22, 23 is in contact with an outer peripheral surface of the housing 8, and the diameters thereof are elastically expanded in a direction in which each radius of curvature increases. Accordingly, the lens cap 20 holds the housing 8 from both sides by the force of the cylindrical body 21 trying to elastically restore its natural state and the force of the pair of arc portions 22, 23 trying to elastically reduce the diameters. As a result, the lens cap 20 is fixed to the housing 8.

Next, the operator covers one of the upper part and the lower part of the surgical microscope 1 with the first drape 51, and covers the other of the upper part and the lower part of the surgical microscope 1 with the second drape 52. Furthermore, the operator ties the drape body 50 to the surgical microscope 1 by winding the strings 53a, 53b, 54a, 54b, 55a, 55b around the surgical microscope 1 and tying them in a state where the side of the first drape 51 and that of the second drape 52 are overlapped with each other. As a result, the surgical microscope 1 is covered with the drape body 50 together with the lens cap 20.

Next, the operator fixes the drape body 50 to the eyepiece lens 7 with a rubber band or the like, and cuts the portion of the drape body 50 in accordance with the outer diameter of the eyepiece lens. Finally, the operator adjusts the inclination angle of the protective lens 30 with respect to the optical axis L to an angle at which the surgical field can be easily observed.

According to the present embodiment, for example, the following operations and effects can be obtained.

According to the present embodiment descried above, the drape body 50 is fixed to the protective lens 30 attached to the distal end (distal end at a side closer to the surgical field) of the lens cap 20. Therefore, the lens cap 20 attached to the housing 8 is accommodated inside the drape body 50 covering the surgical microscope 1. Furthermore, since the inclination angle of the protective lens 30 with respect to the optical axis L is changeable, by approaching the inclination angle of the protective lens 30 to 90°, it is possible to space the protective lens 30 apart from the surgical field. As a result, a surgical manipulation space for the operator can be secured between the objective lens 6 and the surgical field.

As described above, according to the microscope drape 10 of the present embodiment, it is possible to secure a space sufficient for performing surgical manipulation between the objective lens 6 and the surgical field, and prevent the operator from causing a problem in the surgery due to reflection and/or glare.

Furthermore, according to the present embodiment, since a concavo-convex portion into which the eyepiece lens 7 is inserted is not provided in the drape body 50, the eyepiece lens 7 can be covered at an arbitrary position of the drape body 50. As a result, the microscope drape 10 according to the present embodiment can be applied to various types of the surgical microscope 1 in which relative positions of the objective lens 6 and the eyepiece lens 7 are different therebetween. Meanwhile, the drape body 50 may be provided with bag-shaped concavo-convex portions into which the objective lens 6 and the eyepiece lens 7 are inserted.

Still further, according to the present embodiment, since the drape body 50 is tied to the surgical microscope 1 by the strings 53a, 53b, 54a, 54b, 55a, 55b in a state where the side of the first drape 51 and that of the second drape 52 are overlapped with each other, an operation of covering the surgical microscope 1 is simplified as compared with a case of a bag-shaped drape body. Meanwhile, the shape of the drape body 50 is not limited to the example described above, but may be any shape such as like a bag.

Still further, according to the present embodiment, the lens cap 20 can be attached to various types of the housing 8 which are different in diameter. Accordingly, it is not necessary to prepare the microscope drape 10 dedicated to each of various types of the surgical microscope 1 in which diameters of each housing 8 differ therebetween. As a result, the microscope drape 10 having high versatility can be obtained. Meanwhile, the specific structure of the lens cap 20 that can be attached to various types of the housing 8 which are different in diameter is not limited to the example described above of the present embodiment. Hereinafter, lens caps 60, 70, 80 according to first to third modifications will be described.

[First Modification]

Figure 5:
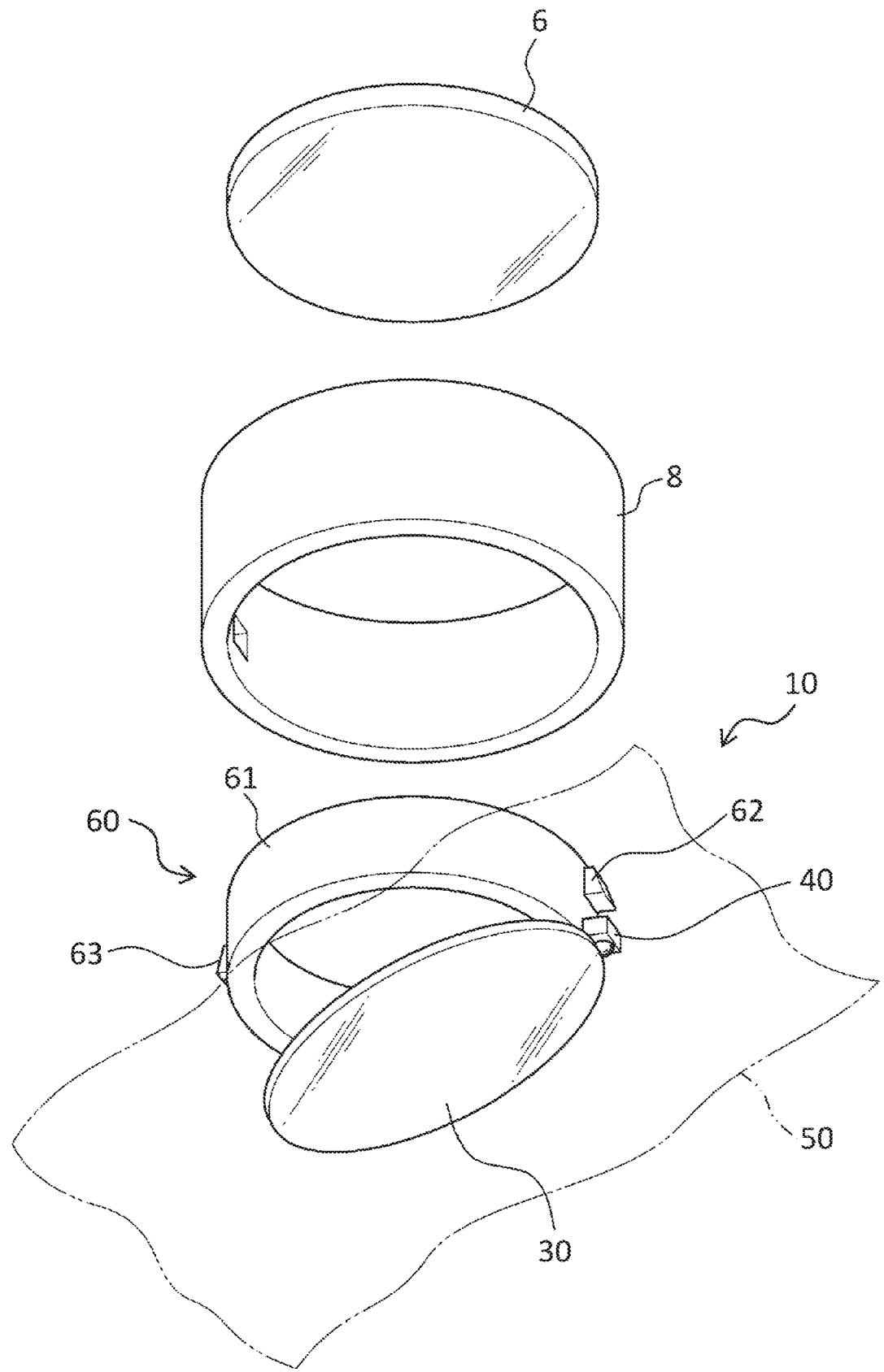
FIG. 5 is a perspective diagram of a lens cap according to a first modification.

FIG. 5 is a perspective diagram of the lens cap 60 according to a first modification. In the following, differences from the embodiment described above will be focused on while omitting to describe common points therewith. The lens cap 60 according to the first modification includes a circular cylindrical body 61 and a plurality of locking projections 62.

The cross-sectional shape of the circular cylindrical body 61 is a true circle. In addition, an outer diameter of the circular cylindrical body 61 is smaller than an inner diameter of the housing 8. The protective lens 30 is attached to a distal end of the circular cylindrical body (end at a side closer to the surgical field) via the joint 40.

The locking projections 62, 63 protrude outwardly from an outer peripheral surface of the circular cylindrical body 61 in the radial direction. Furthermore, the locking projections 62, 63 are arranged at equal intervals in the circumferential direction of the circular cylindrical body 61. Still further, the locking projections 62, 63 are retractable with respect to the circular cylindrical body 61 and biased in a direction of protruding from the circular cylindrical body 61 by a biasing member (spring), etc.

The operator inserts the circular cylindrical body 61 into the housing 8 from an end portion of the housing 8 which is opposite to a side on which the protective lens 30 is attached in a state where the locking projections 62, 63 are depressed in the circular cylindrical body 61. Next, the operator removes the force that has depressed the locking projections 62, 63. Thus, the locking projections 62, 63 protruding from the circular cylindrical body 61 enters a circumferential groove provided inside the housing 8, whereby the circular cylindrical body 61 is locked in the housing 8. As a result, the lens cap 60 is secured to the housing 8.

[Second Modification]

Figure 6:
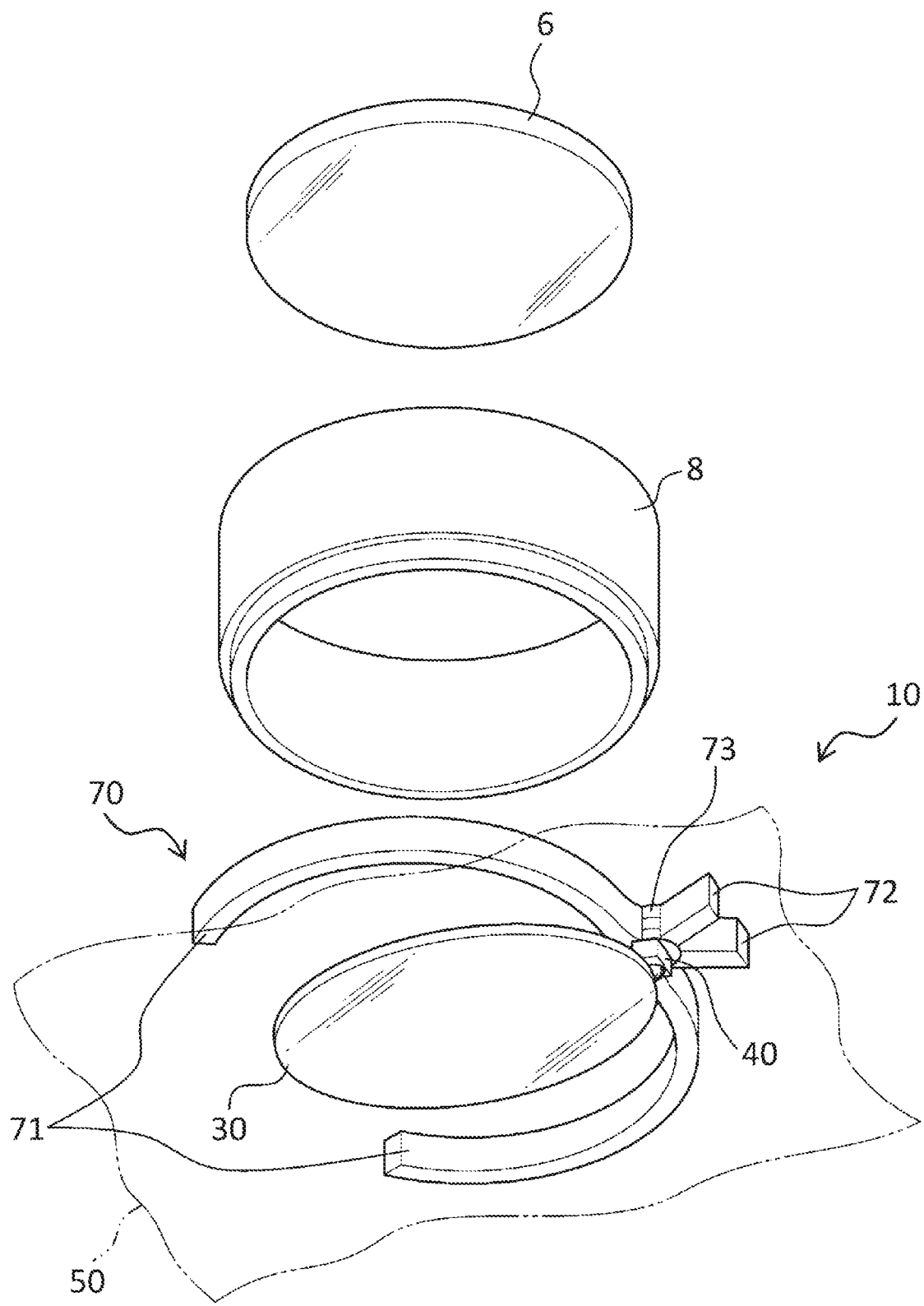
FIG. 6 is a perspective diagram of a lens cap according to a second modification.

FIG. 6 is a perspective diagram of the lens cap 70 according to a second modification. In the following, differences from the embodiment described above will be focused on while omitting to describe common points therewith. The lens cap 70 according to the second modification includes a clip portion 71, a grip portion 72, and a coil spring (biasing member) 73.

The clip portion 71 has a ring-shaped outer form in its natural state. The clip portion 71 is formed to be opened and closed at one position provided on its circumference (end portion opposite to the grip portion 72). The grip portion 72 opens the clip portion 71 by being gripped by the operator. The coil spring 73 biases the clip portion 71 in a closing direction. The protective lens 30 is attached to a boundary portion between the clip portion 71 and the grip portion 72 via the joint 40.

The operator grips the grip portion 72 to open the clip portion 71, and inserts the housing 8 in the clip portion 71 in an opened state. Next, the operator releases the grip portion 72. Thus, the clip portion 71 which has closed by the biasing force of the coil spring 73 abuts against the outer peripheral surface of the housing 8. As a result, the lens cap 70 is secured to the housing 8.

[Third Modification]

Figure 7:
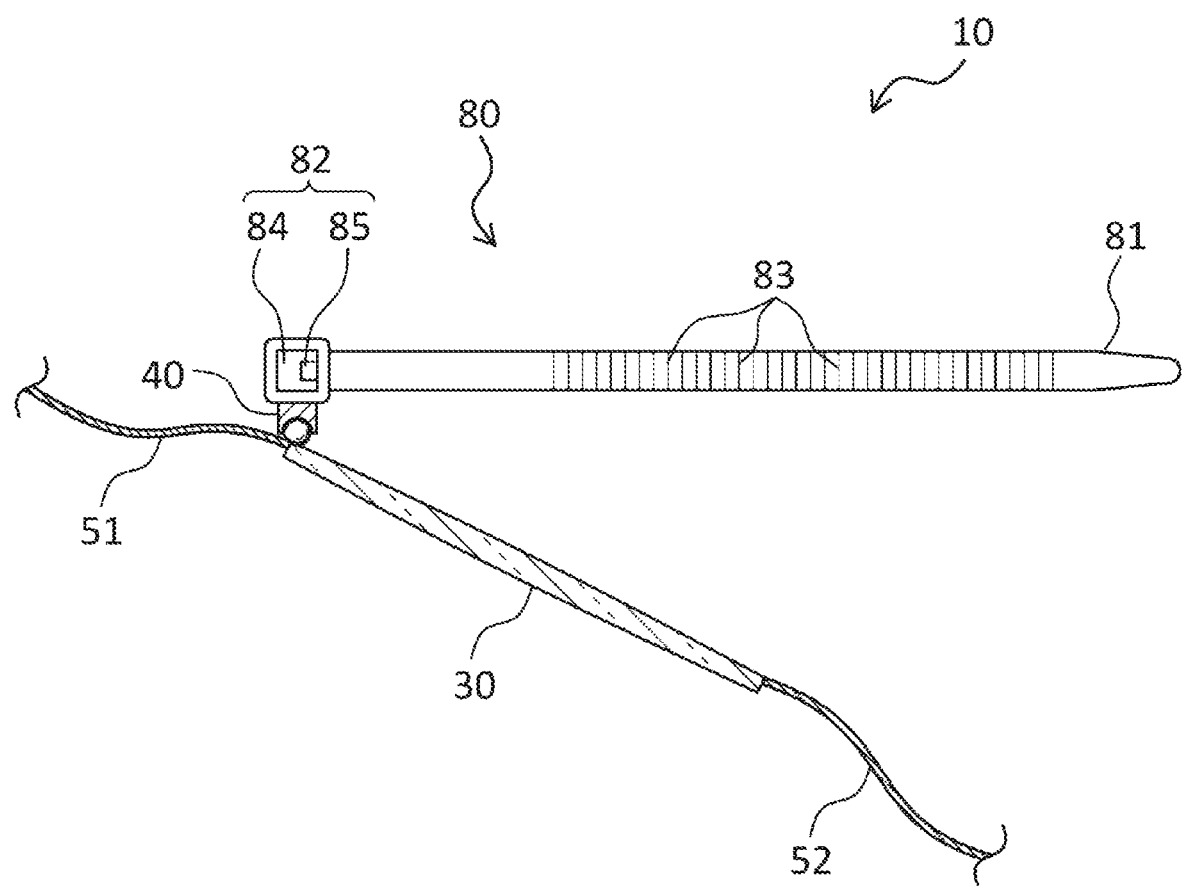
FIG. 7 is a schematic diagram of a lens cap according to a third modification.

FIG. 7 is a schematic diagram of the lens cap 80 according to a third modification. In the following, differences from the embodiment described above will be focused on while omitting to describe common points therewith. The lens cap 80 according to the third modification includes a belt 81 and a head 82. The lens cap 80 is a so-called "zip tie".

The belt 81 has a long strip-shaped outer form. A surface of the belt 81 is provided with a plurality of teeth 83. The head 82 is attached to a base end of the belt 81. The head 82 includes a through hole 84 into which a tip of the belt 81 is inserted, and a locking claw 85 provided in the through hole 84. The protective lens 30 is attached to the head 82 via the joint 40.

The lens cap 80 according to the third modification is provided in a state where the belt 81 is inserted into the through hole 84 to form the lens cap 80 into an elliptical ring shape. It is desirable that the diameter when the ellipse is deformed into a true circle is slightly greater (e.g., 95 mm to 100 mm) than a maximum diameter (e.g., 90 mm) of the housing 8.

The operator fits the lens cap 80 deformed into a shape close to a true circle onto the housing 8. Next, the operator tightens the belt 81 until it is in close contact with the outer peripheral surface of the housing 8 to fix the belt 81 to the housing 8. The belt 81 passes through the head 82 while the teeth 83 ride over the locking claw 85. As a result, the lens cap 80 is secured to the housing 8.

When the belt 81 enters the through hole 84, the teeth 83 can ride over the locking claw 85. On the other hand, when the force of a direction of withdrawing the belt 81 from the through hole 84 is applied to the belt 81, the teeth 83 are locked by the locking claw 85 and thus prevent the belt 81 from being withdrawn from the through hole 84. When removing the microscope drape 10 from the surgical microscope 1, the operator may cut the belt 81.

[Fourth Modification]

FIG. 8 is a schematic diagram of a lens cap 90 according to a fourth modification. In the following, differences from the embodiment described above will be focused on while omitting to describe common points therewith. As illustrated in FIG. 8A, the lens cap 90 according to the fourth modification includes an arc portion 91 and a pair of guiding portions 92, 93.

The arc portion 91 has an arc shape in which a part of a circle in a circumferential direction is opened. In other words, the arc portion 91 has a so-called "C shape". The arc portion 91 includes the radius of curvature which is the smallest in its natural state, and is elastically deformable in a direction of increasing the radius of curvature. The joint 40 is provided on an opposite side of the opened portion across the center of the arc portion 91.

Each of the guiding portions 92, 93 is provided on each of a pair of distal ends of the arc portion 91. The guiding portions 92, 93 protrude outwardly in the radial direction from each of the distal ends of the arc portion (in other words, in the direction opposite to the center of the arc portion 91). Furthermore, the guiding portions 92, 93 form a tapered shape in which a distance therebetween is gradually widened from base end sides (connecting portions with the arc portion 91) toward distal end sides.

Figure 8A:
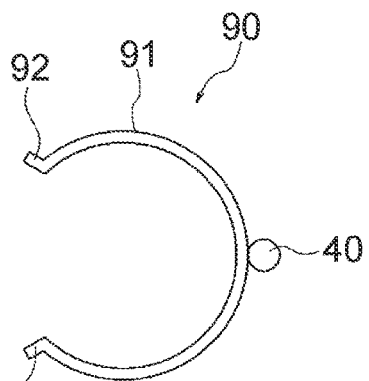
FIG. 8A is a schematic diagram of a lens cap according to a fourth modification.
Figure 8B:
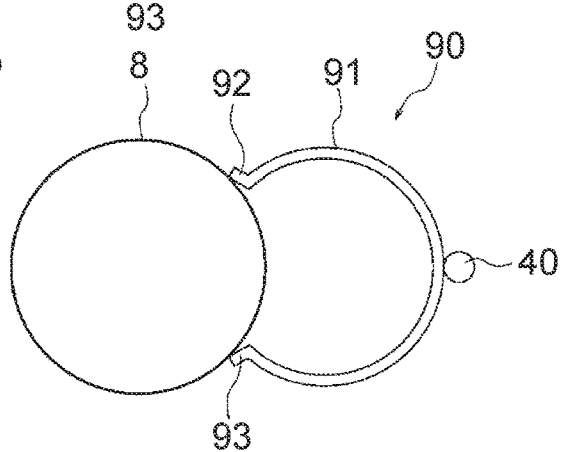
FIG. 8B illustrates a process of attaching the lens cap according to the fourth modification to a housing.

The lens cap 90 according to the fourth modification is attached to the housing 8 by the following procedure. First, as illustrated in FIG. 8B, the guiding portions 92, 93 are pressed against a side surface of the housing 8. Thus, the housing 8 is guided by the guiding portions 92, 93 having the tapered shape, and enters the inside of the arc portion 91. In the process of receiving the housing 8, the arc portion 91 is elastically deformed in a direction of increasing the radius of curvature.

Figure 8C:
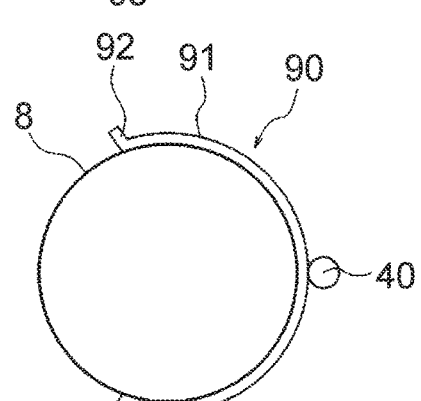
FIG. 8C illustrates a state where the lens cap according to the fourth modification is attached to a housing having a large diameter.
Figure 8D:
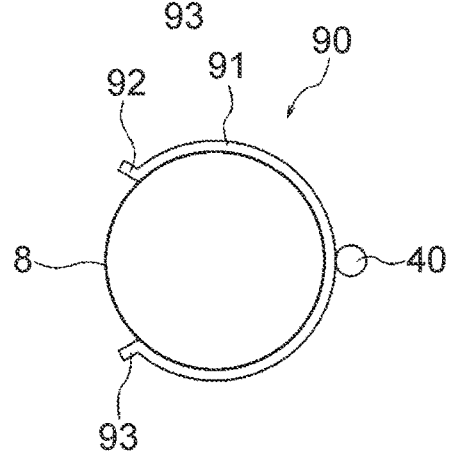
FIG. 8D illustrates a state where the lens cap according to the fourth modification is attached to a housing having a small diameter.

Then, as illustrated in FIG. 8C and FIG. 8D, when the housing 8 completely enters the inside of the arc portion 91, the arc portion 91 is in contact with the outer peripheral surface of the housing 8 in a state of being elastically expanded. At this time, the lens cap 90 holds the housing 8 by the force of the arc portion 91 trying to elastically restore its shape in a direction of reducing the radius of curvature. As a result, the lens cap 90 according to the fourth modification can be attached to various types of the housing 8 which are different in diameter.

[Fifth Modification]

FIG. 9 is a schematic diagram of a lens cap 100 according to a fifth modification. In the following, differences from the embodiment described above will be focused on while omitting to describe common points therewith. As illustrated in the FIG. 9A, the lens cap 100 according to the fifth modification includes a pair of arc portions 101, 102 and a pair of bellows portions 103, 104.

Each of the arc portions 101, 102 has an arc-shaped outer form which corresponds to a part of a circle. The arc portions 101, 102 are disposed opposite to each other across the center of the lens cap 100. In other words, the arc portions 101, 102 are disposed at predetermined intervals in the circumferential direction of the lens cap 100. The joint 40 is provided on one of the arc portions 101, 102 (in the example of FIG. 9, provided on the arc portion 101).

Each of the bellows portions 103, 104 includes a bellows structure in which upwardly folded portions and downwardly folded portions are alternately arranged. The bellows portions 103, 104 are disposed to face each other across the center of the lens cap 100. In other words, the bellows portions 103, 104 connect ends of the arc portions 101, 102 to each other. That is, the arc portion 101, the bellows portion 103, the arc portion 102, and the bellows portion 104 are continuous in the circumferential direction to form the ring-shaped lens cap 100. In this connection, one of the bellows portions 103, 104 can be omitted as long as the lens cap 100 is provided with a bellows portion at least on one position in the circumferential direction. The bellows portions 103, 104 may be formed of elastic rubber, etc.

The bellows portions 103, 104 are elastically deformable in a direction of reducing the height of the upwardly folded portions and the downwardly folded portions. In other words, elastic deformability of the lens cap 100 in a direction of widening the distance between the pair of arc portions 101, 102 is higher than that in a direction of widening a distance between the pair of bellows portions 103, 104.

Figure 9A:
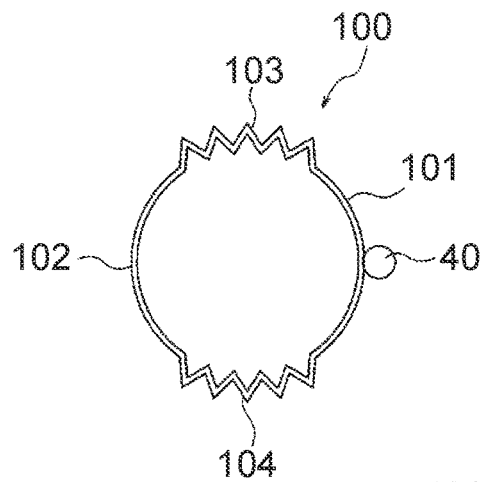
FIG. 9A is a schematic diagram of a lens cap according to a fifth modification.
Figure 9B:
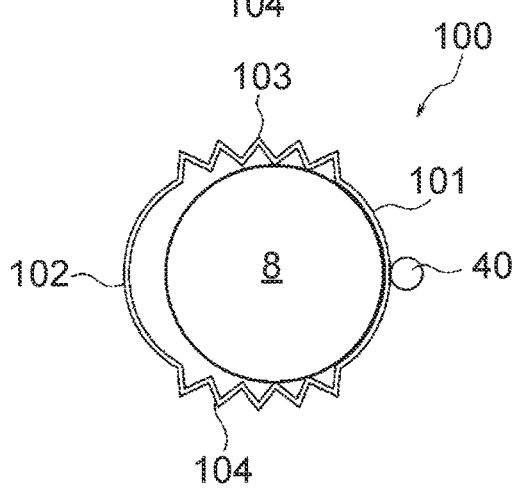
FIG. 9B illustrates a process of attaching the lens cap according to the fifth modification to a housing.

The lens cap 100 according to the fifth modification is attached to the housing 8 by the following procedure. First, the arc portion 101 on which the joint 40 is provided is hooked on the outer peripheral surface of the housing 8. Next, as illustrated in FIG. 9B, the arc portion 102 is pulled in a direction of separating from the arc portion 101 to elastically deform the bellows portions 103, 104 in the direction of reducing the height of the upwardly folded portions and the downwardly folded portions.

Figure 9C:
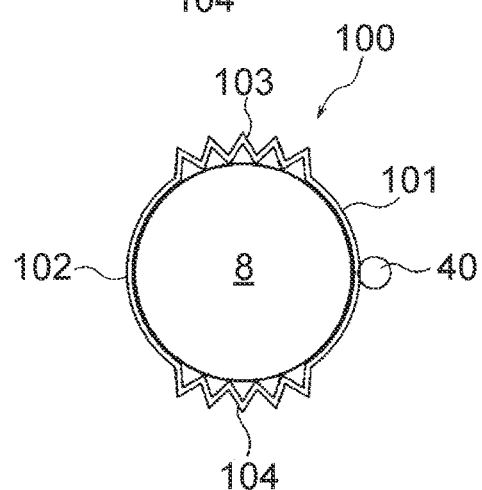
FIG. 9C illustrates a state where the lens cap according to the fifth modification is attached to a housing having a small diameter.
Figure 9D:
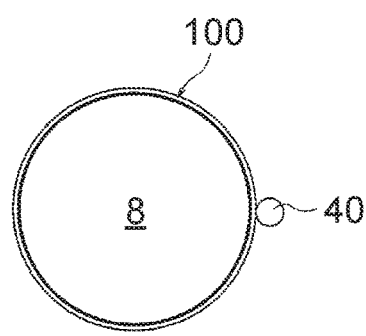
FIG. 9D illustrates a state where the lens cap according to the fifth modification is attached to a housing having a large diameter.

Then, as illustrated in FIG. 9C and FIG. 9D, the force of pulling the arc portion 102 is removed in a state where the housing 8 enters the inside of the lens cap 100, which makes the lens cap 100 in contact with the outer peripheral surface of the housing 8. At this time, the lens cap 100 holds the housing 8 by the force of the bellows portions 103, 104 trying to elastically restore their original state. As a result, the lens cap 100 according to the fifth modification can be attached to various types of the housing 8 which are different in diameter. Furthermore, as illustrated in FIG. 9D, when the lens cap 100 is attached to the housing 8 having a large diameter, the lens cap 100 is in contact with the outer peripheral surface of the housing 8 in a state where the upwardly folded portions and the downwardly folded portions of the bellows portions 103, 104 are elongated.

[Sixth Modification]

Figure 10A:
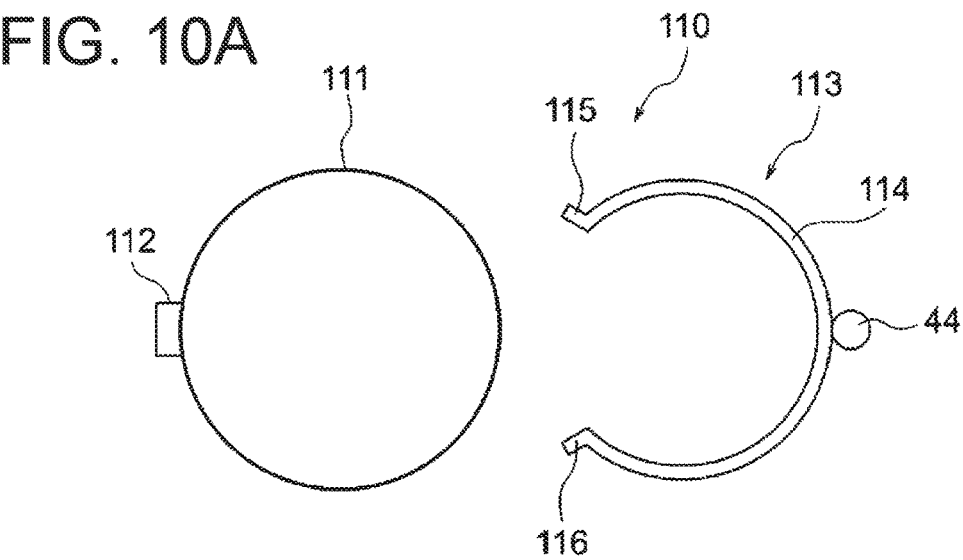
FIG. 10A is an exploded diagram of a protective lens unit according to a sixth modification.

FIG. 10 is a schematic diagram of a protective lens unit 110 according to a sixth modification. In the following, differences from the embodiment described above will be focused on while omitting to describe common points therewith. The protective lens unit 110 according to the sixth modification can be applied to any of the embodiment described above and the first to fifth modifications. As illustrated in FIG. 10A, the protective lens unit 110 according to the sixth modification includes a lens body 111, a tab 112, and a lens holding portion 113.

The tab 112 is provided on a part of the lens body 111 in its circumferential direction, and protrudes outwardly in the radial direction from an outer peripheral portion of the lens body 111. The tab 112 is, for example, integrally formed with the lens body 111. The tab 112 functions as a grip portion at the time of attaching/detaching the lens body 111 to or from the lens holding portion 113.

The lens holding portion 113 includes an arc portion 114 and a pair of guiding portions 115, 116. The structure of the lens holding portion 113 is common to that of the lens cap 90 according to the fourth modification. The tip of the rod 44 of the joint 40 is connected to the arc portion 114 on a side opposite to an opened portion. In addition, the drape body 50 is connected (welded) to the lens holding portion 113.

Figure 10B:
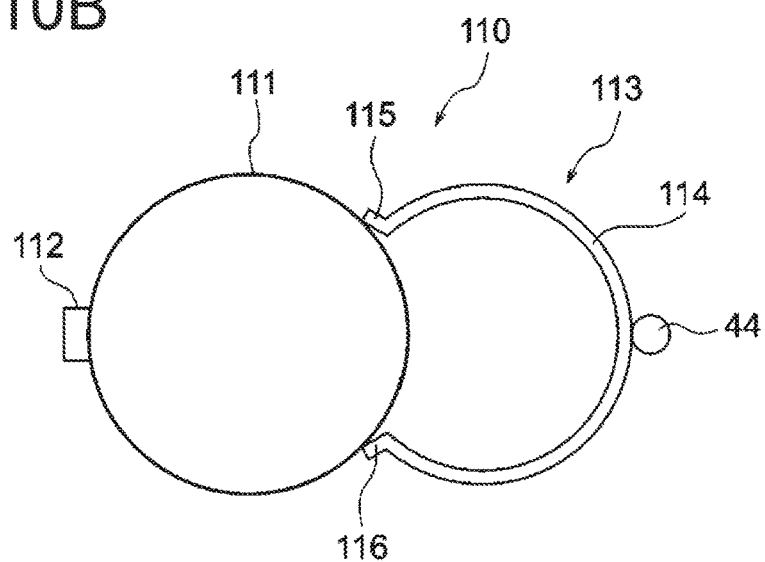
FIG. 10B illustrates a process of attaching a protective lens according to the sixth modification to a lens holding portion.

The lens body 111 according to the sixth modification is attached/detached to or from the lens holding portion 113 by the following procedure. First, as illustrated in FIG. 10B, the tab 112 is gripped to push the lens body 111 against the guiding portions 115, 116. Thus, the lens body 111 is guided by the tapered-shaped guiding portions 115, 116, and enters the inside of the arc portion 114. The arc portion 114 is elastically deformed in a direction of increasing the radius of curvature in the process of receiving the lens body 111.

Figure 10C:
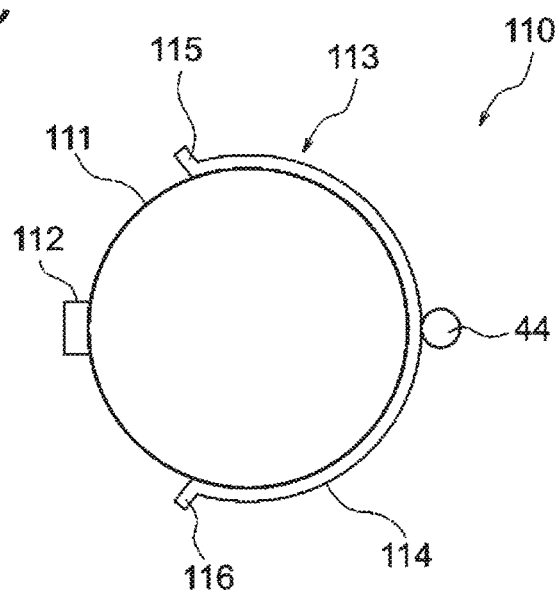
FIG. 10C illustrates a state where the protective lens according to the sixth modification is attached to the lens holding portion.

Then, as illustrated in FIG. 10C, when the lens body 111 completely enters the inside of the arc portion 114, the arc portion 114 is in contact with an outer peripheral surface of the lens body 111 in a state where the diameter thereof is elastically expanded. At this time, the lens holding portion 113 holds the lens body 111 by the force of the arc portion 114 trying to elastically restore its shape in a direction of reducing the radius of curvature. The lens body 111 can be pulled out from the lens holding portion 113 by pulling the tab 112 from the state illustrated in FIG. 10C.

Since the lens body 111 is disposed at a position close to the surgical field, there is a case that splashed blood, a washing liquid, or the like adheres thereto. In addition, at the time of adjusting an angle of the lens body 111, there is a case that dirt on a surface of a glove adheres to the lens body 111. According to the protective lens unit 110 of the sixth modification, it is possible to easily attach/detach the lens body 111, thereby always ensuring a clear view.

[Seventh Modification]

Figure 11:
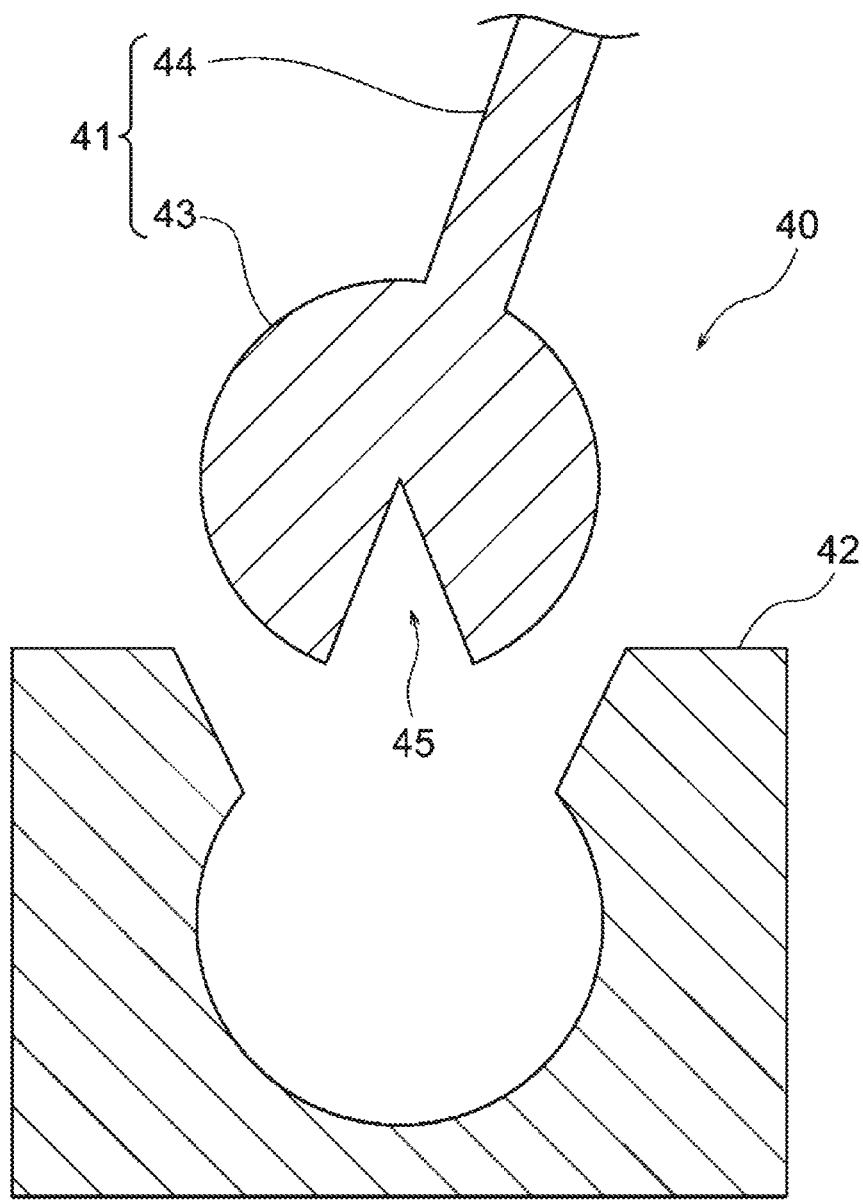
FIG. 11 is a cross-section diagram of a joint according to a seventh modification.

FIG. 11 is a cross-section diagram of the joint 40 according to a seventh modification. In the following, differences from the embodiment described above will be focused on while omitting to describe common points therewith. The joint 40 according to the seventh modification can be applied to any of the embodiment described above and the first to sixth modifications.

In the seventh modification, the socket 42 is integrally formed with the lens caps 20, 60, 70, 80, 90, 100. The ball stud 41, that is the ball 43 and the rod 44 are integrally formed but separately from the socket 42. In the sixth modification, the lens holding portion 32 and the ball stud 41 may be integrally formed.

Furthermore, the ball 43 according to the seventh modification is provided with a notch 45. The notch 45 has, for example, a shape in which a part of the ball 43 is so-called "cut into a wedge". More specifically, the notch 45 has a shape in which a part of the ball 43 is cut along cutting lines starting from two different points on a surface of the ball 43 to the same imaginary lines passing through the inside of the ball 43. The notch 45 is provided to elastically deform the ball 43 in a direction of reducing the diameter. It should be noted that the ball 43 may be provided with a single or a plurality of notches 45, and an angle and size thereof are not limited to the example illustrated in FIG. 11.

The diameter of the ball 43 is greater than an opening in the socket 42. Accordingly, the ball 43 is inserted into the socket 42 in a state of being elastically compressed in a direction of narrowing the notch 45. The ball 43 is elastically restored inside the socket 42, which prevents the ball 43 from falling out from the socket 42.

REFERENCE SIGNS LIST

1: surgical microscope; 2, 3, 4, 5: arm; 6: objective lens; 7: eyepiece lens; 8: housing; 10: microscope drape; 21: cylindrical body; 20, 60, 70, 80, 90, 100: lens cap; 22, 23, 91, 101, 102, 114: arc portion; 30: protective lens; 40: joint; 41: ball stud; 42: socket; 43: ball; 44: rod; 45: notch; 50: drape body; 51: first drape; 52: second drape; 53a, 53b, 54a, 54b, 55a, 55b: string (tying portion); 61: cylindrical column; 62, 63: locking projection; 71: clip portion; 72: grip portion; 73: coil spring; 81: belt; 82: head; 83: teeth; 84: through hole; 85: locking claw; 92, 93, 115, 116: guiding portion; 103, 104: bellows portion; 110: protective lens unit; 111: lens body; 112: tab; 113: lens holding portion

The invention claimed is:

1. A microscope drape for covering a surgical microscope, comprising:
   a lens cap that is attached to or detached from a housing of an objective lens of the surgical microscope;
   a protective lens that is attached to a distal end of the lens cap in a state of being inclined with respect to an optical axis of the objective lens to protect the objective lens;
   a drape body that is directly attached to an outer periphery of the protective lens to cover, together with the lens cap, the surgical microscope; and
   a joint that supports the protective lens with respect to the lens cap so as to change an inclination angle of the protective lens with respect to the optical axis,
   wherein the lens cap has an outer shape formed to be deformable so as to be attached to various types of the housing which are different in diameter, and
   wherein the drape body is a sheet-like member.

2. The microscope drape according to claim 1, wherein the lens cap includes:
   a cylindrical body of which a cross-section has a flat circular shape with a major axis and a minor axis, the cylindrical body being formed to be elastically deformable so as to change length of the major axis and the minor axis; and
   a pair of arc portions, each of the pair of arc portions being formed to have an arc shape which is elastically deformable so as to increase or reduce a radius of curvature thereof, the pair of arc portions being formed to be fixed to an inside of the cylindrical body such that inner peripheral surfaces thereof face each other in a direction of the minor axis.

3. The microscope drape according to claim 2, wherein the cylindrical body of the lens cap is elastically compressed in a direction of the major axis, the lens cap is fitted onto the housing, and thereafter, compressive force is removed so that each of the inner peripheral surfaces of the pair of arc portions in a state where diameters thereof are elastically expanded is in contact with an outer peripheral surface of the objective lens, so as to attach the lens cap to the objective lens.

4. The microscope drape according to claim 2, wherein the cross-section of the cylindrical body is a cross-section perpendicular to the optical axis which has, in a natural state, the flat circular shape, wherein the minor axis is shorter than the major axis.

5. The microscope drape according to claim 1, wherein the lens cap includes:
   a circular cylindrical body to be inserted into the housing; and
   a plurality of locking projections that protrudes from an outer peripheral surface of the circular cylindrical body to lock the circular cylindrical body on an inside of the housing.

6. The microscope drape according to claim 1, wherein the lens cap includes:
   a ring-shaped clip portion of which one position provided on a circumference thereof is openable/closable;
   a grip portion that opens the clip portion by being gripped; and
   a biasing member that biases the clip portion in a direction of closing the clip portion.

7. The microscope drape according to claim 1, wherein the lens cap includes:
   a long belt; and
   a head that is attached to a base end of the belt, and the head includes:
   a through hole into which a tip of the belt wound around an outer peripheral surface of the housing is inserted; and
   a locking claw that locks the belt which has been inserted into the through hole.

8. The microscope drape according to claim 1, wherein the lens cap includes:
   a pair of arc portions disposed to face each other across a center of the lens cap; and
   a pair of bellows portions, each of the pair of bellows portions being to formed to have a bellows structure in which upwardly folded portions and downwardly folded portions are alternately arranged, and connect ends of a pair of the arc portions to each other.

9. The microscope drape according to claim 1, wherein the protective lens includes and unitizes:
   a lens body; and
   a lens holding portion to which the drape body and the joint are attached, the lens holding portion being formed to removably support the lens body.

10. The microscope drape according to claim 1, wherein the joint includes:
    a ball stud that has a ball and a rod projecting from the ball; and
    a socket that rotatably supports the ball, and
    the ball is provided with a notch so as to elastically deform the ball in a direction of reducing a diameter thereof.

11. The microscope drape according to claim 1, wherein the drape body is a smooth sheet without a concavo-convex portion into which an eyepiece lens of the surgical microscope is inserted.

12. The microscope drape according to claim 1, wherein the drape body includes:
    a first drape that covers one of upper and lower sides of the surgical microscope;
    a second drape that covers the other of the upper and lower sides of the surgical microscope; and a tying portion that ties the first drape and the second drape to the surgical microscope in a state where outer edges of the first drape and the second drape are overlapped with each other.

13. A microscope drape for covering a surgical microscope, comprising:
- a lens cap that is attached to or detached from a housing of an objective lens of the surgical microscope;
- a protective lens that is attached to a distal end of the lens cap in a state of being inclined with respect to an optical axis of the objective lens to protect the objective lens; and
- a drape body that is directly attached to an outer periphery of the protective lens to cover, together with the lens cap, the surgical microscope,
- wherein the lens cap includes an arc portion having a C shape in which a part of a circle in a circumferential direction is opened, the arc portion being formed such that a radius of curvature thereof is the smallest in a natural state, while being elastically deformable in a direction of increasing the radius of curvature.

14. The microscope drape according to claim 13, wherein the lens cap includes a pair of guiding portions that protrude from each of a pair of distal ends of the arc portion outwardly in a radial direction of the arc portion so as to widen a distance therebetween.

15. The microscope drape according to claim 13, further comprising a joint that supports the protective lens with respect to the lens cap so as to change an inclination angle of the protective lens with respect to the optical axis,
- wherein the lens cap has an outer shape formed to be deformable so as to be attached to various types of the housing which are different in diameter.

* * * * *